United States Patent
Takemoto

(10) Patent No.: US 10,383,802 B2
(45) Date of Patent: Aug. 20, 2019

(54) CURABLE RESIN COMPOSITION

(71) Applicant: ThreeBond Co., Ltd., Hachioji-shi, Tokyo (JP)

(72) Inventor: Koichi Takemoto, Hachioji (JP)

(73) Assignee: THREEBOND CO., LTD., Hachioji-Shi, Tokyo (JP)

( * ) Notice: Subject to any disclaimer, the term of this patent is extended or adjusted under 35 U.S.C. 154(b) by 0 days.

(21) Appl. No.: 15/326,880

(22) PCT Filed: Jul. 10, 2015

(86) PCT No.: PCT/JP2015/069941
§ 371 (c)(1),
(2) Date: Jan. 17, 2017

(87) PCT Pub. No.: WO2016/009969
PCT Pub. Date: Jan. 21, 2016

(65) Prior Publication Data
US 2017/0209351 A1 Jul. 27, 2017

(30) Foreign Application Priority Data
Jul. 17, 2014 (JP) .................................. 2014-146472

(51) Int. Cl.
| | |
|---|---|
| *A61K 8/37* | (2006.01) |
| *A61Q 3/02* | (2006.01) |
| *A61K 8/87* | (2006.01) |
| *A61K 8/55* | (2006.01) |
| *A61K 8/25* | (2006.01) |
| *A61K 8/81* | (2006.01) |

(52) U.S. Cl.
CPC ................ *A61K 8/37* (2013.01); *A61K 8/25* (2013.01); *A61K 8/375* (2013.01); *A61K 8/55* (2013.01); *A61K 8/8152* (2013.01); *A61K 8/87* (2013.01); *A61Q 3/02* (2013.01); *A61K 2800/26* (2013.01); *A61K 2800/81* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 2002/0045126 A1* | 4/2002 | Watanabe | G03F 7/0037 430/280.1 |
| 2010/0008876 A1 | 1/2010 | Tanaka et al. | |
| 2012/0071579 A1* | 3/2012 | Kitano | C09J 4/06 522/96 |
| 2012/0118314 A1 | 5/2012 | Haile | |
| 2014/0261512 A1* | 9/2014 | Nordstrom | A61Q 3/02 132/200 |
| 2015/0352032 A1* | 12/2015 | Abe | A61Q 3/00 132/200 |

FOREIGN PATENT DOCUMENTS

| | | |
|---|---|---|
| FR | 2998787 A1 | 6/2014 |
| JP | H02-19313 A | 1/1990 |
| JP | 2006-312596 A | 11/2006 |
| JP | 2010-037330 A | 2/2010 |
| JP | 2011-020956 A | 2/2011 |
| JP | 2011-032259 A | 2/2011 |
| JP | 2013-043853 A | 3/2013 |
| JP | 5636533 B1 | 12/2014 |
| WO | 2011/016531 A1 | 2/2011 |

OTHER PUBLICATIONS

Koyama, Yutaka. English translation of JP2013043853; acessed Nov. 14, 2017 (Year: 2013).*
Taiwan Patent Office, "Office Action for Taiwanese Patent Application No. 104122275," dated Aug. 27, 2018.
PCT/ISA/210, "International Search Report for International Application No. PCT/JP2015/069941" dated Oct. 13, 2015.

* cited by examiner

*Primary Examiner* — Nicole P Babson
(74) *Attorney, Agent, or Firm* — Manabu Kanesaka

(57) ABSTRACT

Using a curable resin composition including the following (A) to (E) configurations, which is excellent in adhesiveness to nails and curing reactivity, and a cured product of which has a certain flexibility, makes it possible to form a coating aiming for protection, decoration, and the like of nails with favorable followability to the nails: (A) 100 parts by mass of a polymer having a urethane structure in molecule and containing acrylic functional groups at both terminals of a molecular chain, (B) 1 to 35 parts by mass of a trifunctional acrylic functional compound of a specific structure, (C) 15 to 75 parts by mass of a compound containing an acrylic functional group having an aliphatic ring structure, (D) 1 to 35 parts by mass of a compound containing an acrylic functional group having an aliphatic chain structure, and (E) 0.5 to 13.5 parts by mass of a photopolymerization initiator.

18 Claims, 1 Drawing Sheet

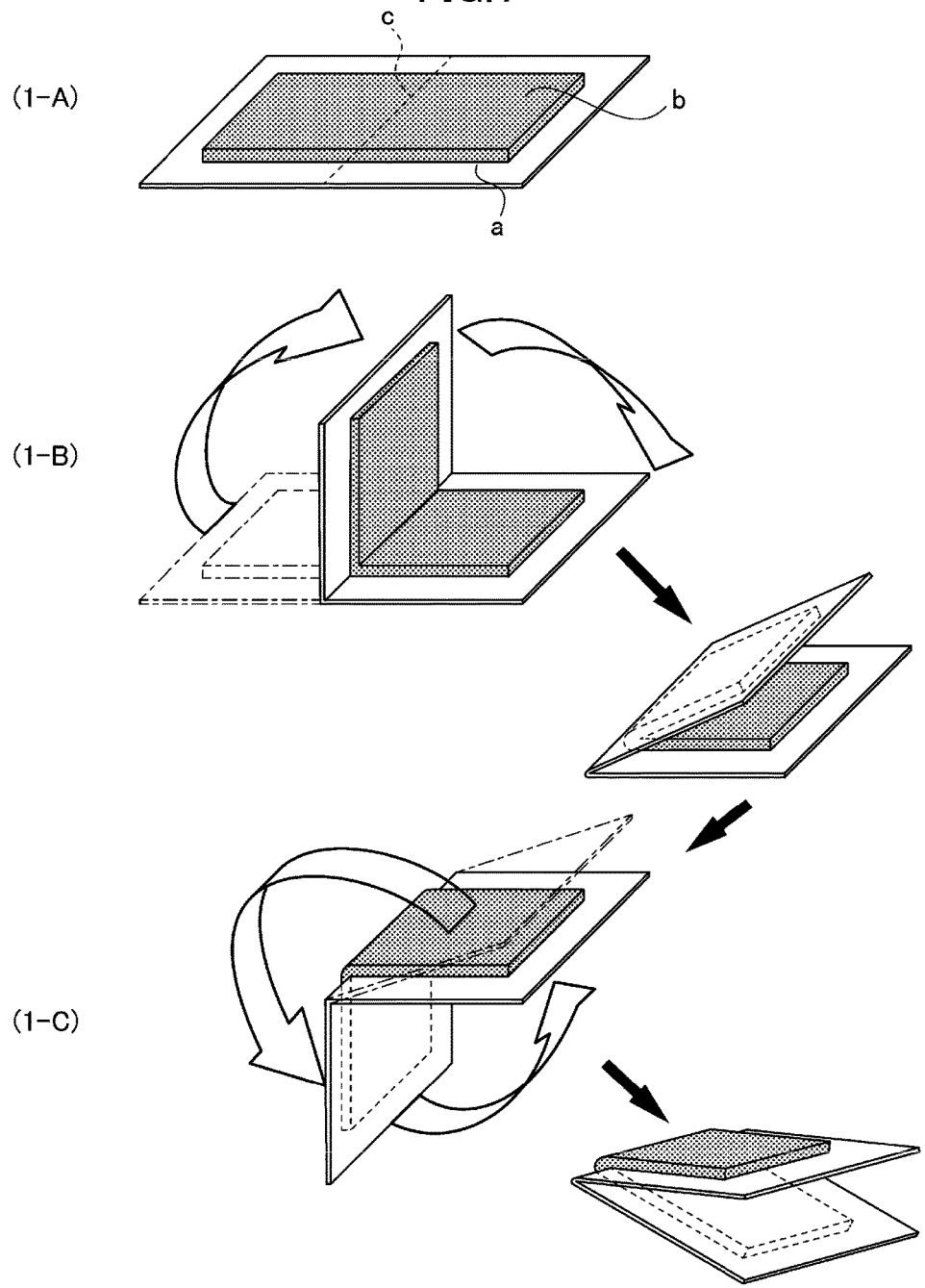

CURABLE RESIN COMPOSITION

RELATED APPLICATIONS

The present application is National Phase of International Application No. PCT/JP2015/069941 filed Jul. 10, 2015, and claims priority from Japanese Application No. 2014-146472, filed Jul. 17, 2014, the disclosure of which is hereby incorporated by reference herein in its entirety.

TECHNICAL FIELD

The present invention relates to a curable resin composition (a nail coating agent) suitable for coating nails of humans and/or mammals, and more particularly relates to a curable resin composition for coating nails that is excellent in adhesiveness and curability and that is unlikely to cause defects in external appearance or to be detached from the nails, when being used to coat the nails for decorating, protecting, or reinforcing the nails.

BACKGROUND ART

There have recently been growing consumers' demands for materials for use in so-called manicure, pedicure, and sculpture, which decorate or reinforce nails by applying resin compositions and the like to the nails, for the purpose of decorating the nails, or for the purpose of decorating artificial nails bonded onto nails, or for the purpose of preventing nails from being chipped or peeled due to external forces applied during exercises and the like. Here, the mainstream coating material used for decoration or reinforcement includes those obtained by dissolving nitrocellulose-based lacquers in organic solvents and adding pigments of various color tones to the solutions.

Besides these, various coating materials have been used, including those obtained by adding pigments and plasticizers in systems of alkyd resins and the like. These coating materials provide coatings excellent in gloss in a short period of time when the coating materials are applied to keratins of nails or the like and then organic solvents are evaporated. The coating formed on the nail can be readily wiped off by using an organic solvent such as acetone.

These types of coating materials, however, have poor adhesiveness with natural nails, and thus are easily peeled off and detached off by rubbing or contact with a liquid such as water, after being applied.

To solve such problems in using lacquers, there has recently been used a technique of curing manicure on nails using materials that are curable by chemical reaction.

For example, Patent Literature 1 discloses a curable composition for nail decoration comprising: a polyether urethane acrylate having a mass average molecular weight of 5500 or 8000; a compound having an alicyclic structure and an ethylenic unsaturated group; an acrylic monomer having a hydroxyl group; a photo-radical polymerization initiator; a radical polymerization inhibitor; and the like.

Patent Literature 2 discloses a photocurable manicure composition comprising: a urethane acrylate having a polyester backbone; a hydroxyl group-containing acrylic monomer; a carboxylic acid-modified polyester acrylate; a polyol compound; a photo-radical polymerization initiator; and the like.

Patent Literature 3 discloses an artificial nail composition comprising: an acrylic functional compound having a polyol backbone; an acrylic functional compound having a urethane backbone; photo-radical polymerization initiator; and the like.

Patent Literature 4 discloses a composition for manicure comprising: a urethane acrylate; a trifunctional acrylic monomer; a photo-radical polymerization initiator; and the like.

Patent Literature 5 discloses a color polish for nail manicure, comprising: a polyester urethane acrylate; a bifunctional acrylic monomer having a glycol backbone; an epoxy acrylate; and the like.

CITATION LIST

Patent Literatures

Patent Literature 1: International Publication No. 2011/016531
Patent Literature 2: Japanese Patent Application Laid-open No. 2011-020956
Patent Literature 3: Japanese Patent Application Laid-open No. 2010-037330
Patent Literature 4: Japanese Patent Application Laid-open No. Hei 2-019313
Patent Literature 5: Japanese Patent Application Laid-open No. 2006-312596

SUMMARY OF INVENTION

Technical Problems

Although these techniques have no problems in adhesiveness to nails and curability, these techniques have a problem that the cured product possibly has a too high hardness, causing the cured product to be chipped or cracked, or detached from the nail upon application of an external force to the nail. Moreover, these techniques are poor in external appearance. Against such backgrounds, the present invention provides a curable resin composition that is suitable for covering nails, with which a cured product is excellent in adhesiveness and curability, and has a certain level of flexibility, thus being capable of favorably following nails, and is unlikely to suffer defects in external appearance and to be detached from nails.

Solution to Problems

The present inventors have made studies earnestly to solve the above problems, and have found that the problems can be solved by using a curable resin composition having the following configuration. Specifically, a curable resin composition for coating nails comprises:

(A) 100 parts by mass of a compound having a urethane structure in molecule and containing acrylic functional groups at both terminals of a molecular chain;

(B) 1 to 35 parts by mass of an acrylic functional group-containing compound having the following chemical structure

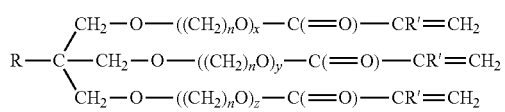

wherein x, y, and z are each independently an integer of 0 to 10 and satisfy x+y+z≤25, R is a functional group selected from alkyl, aryl, haloalkyl, haloaryl, hydroxy alkyl, hydroxy haloalkyl groups each having 1 to 5 carbon atoms, R's are each a hydrogen atom or a functional group selected from alkyl and haloalkyl groups each having 1 to 3 carbon atoms, and may be the same or different, and n is an integer of 1 to 4;

(C) 15 to 75 parts by mass of a compound containing an acrylic functional group having an aliphatic ring structure;

(D) 1 to 35 parts by mass of a compound containing an acrylic functional group having an aliphatic chain structure; and (E) 0.5 to 13.5 parts by mass of a photopolymerization initiator.

In addition, the present invention also includes the following embodiments.

A second embodiment relates to the curable resin composition for coating nails according to the first embodiment, wherein the (A) component comprises an acrylic functional group-containing compound having a polyester backbone and a mass average molecular weight of 1000 to 8000.

A third embodiment relates to the curable resin composition for coating nails according to the first or second embodiment, wherein the (C) component comprises: (c-1) a compound having an aliphatic ring structure and containing two or more acrylic functional groups; and (c-2) a compound having an aliphatic ring structure and containing one acrylic functional group.

A fourth embodiment relates to a cover coating layer formed by applying and curing the curable resin composition for coating nails according to any one of the first to third embodiments on a nail.

A fifth embodiment relates to the cover coating layer according to the fourth embodiment, wherein the cover coating layer is coated on a base coating layer formed on a nail in advance.

A sixth embodiment relates to a nail coating method, comprising the steps of: (1) applying the curable resin composition for coating nails according to any one of the first to third embodiments onto a nail; and curing the applied curable resin composition by applying an active energy ray (light) to the curable resin composition, forming a cured layer.

A seventh embodiment relates to the nail coating method according to the sixth embodiment, wherein the nail to which the curable resin composition for coating nails is applied is coated with a base coating layer in advance, and the step (1) of applying the curable resin composition for coating nails includes applying the curable resin composition for coating nails onto the nail coated with the base coating.

Effects of Invention

Using the curable resin composition for coating nails (nail coating agent) of the present invention makes it possible to provide a cover coating for nails, which is excellent in adhesiveness to nails and curability, and also a high followability, thus having favorable reliability and external appearance. Further, the curable resin composition for coating nails can be favorably utilized as cover coating as top coats or intermediate coats, by being applied on nails subjected to a base coat process (particularly, human nails and/or nails of mammals other than humans).

BRIEF DESCRIPTION OF DRAWING

FIG. 1 is a schematic diagram illustrating how an overcoatability is evaluated.

DESCRIPTION OF EMBODIMENTS

Configuration requirements of the present invention will be described in detail below.

Regarding (A) Compound Having Urethane Structure in Molecule and Containing Acrylic Functional Groups at Both Terminals of Molecular Chain A compound having a urethane structure in molecule and containing acrylic functional groups at both terminals of a molecular chain, used in the present invention, may be a polymer in which a plurality of monomers are polymerized, and for example, a compound having an urethane backbone in a main chain structure and having acrylic functional groups at both terminals of the main chain structure, and the like are known. As such a compound, a compound obtained by reacting a hydroxyl group-containing acrylic compound with a residual isocyanate group contained in a compound structure obtained by reacting a polyol compound and a polyisocyanate compound are with each other is preferably used, for example. Note that the acrylic functional group mentioned in the present invention refers to an acryl group or a methacryl group, which may hereinbelow be referred collectively to as a "(meth)acryl group," and a compound having both functional groups may be referred to as a "(meth)acrylate."

Here, the polyol compound refers to a compound having two or more hydroxyl groups in molecule, and polyester polyols (including polycarbonate polyols), polyether polyols, and polyalkylene polyols may be used, for example. Among these, a polyester diol having a polycarbonate backbone in a main chain structure and having hydroxyl groups at both terminals of the main chain structure may be particularly preferably used from the viewpoints of cure contraction, adhesion, and flexibility. Note that the polyester backbone used herein refers to condensation polymers of diprotic acids and dihydric alcohols, or ring-opened polymers of cyclic ester compounds.

In addition, the polyisocyanate compound refers to a compound having two or more isocyanate groups in molecule. Various diisocyanate compounds such as isophorone diisocyanate, hexamethylene diisocyanate, tolylene diisocyanate, trimethyl hexamethylene diisocyanate, diisocyanatodiphenylmethane, diisocyanate toluene, tetramethyl xylene diisocyanate, diisocyanatodicyclohexylmethane, diphenylmethane diisocyanate, xylylene diisocyanate, and tolylene diisocyanate may be used, for example. Among these, a diisocyanate compound having an alicyclic structure may be particularly preferably used, for example.

As the hydroxyl group-containing acrylic compound, publicly-known (meth)acrylate compounds such as 2-hydroxyethyl (meth)acrylate, 3-hydroxypropyl (meth)acrylate, 2-hydroxypropyl (meth)acrylate, 4-hydroxybutyl (meth)acrylate, 3-hydroxybutyl (meth)acrylate, α,ω-alkylenediol mono(meth)acrylate, and hydroxycyclohexyl (meth)acrylate may be used, for example.

The role of the (A) component in the present invention is not only to play as a base binder in the curable resin composition for coating nails, but also to contribute to the aesthetics by providing an appropriate gloss to the cured product, and to provide an appropriate flexibility to the cured product. From the viewpoints of the workability during application and the flexibility of the cured product, the range of the mass average molecular weight of the (A) component in the present invention is preferably 1000 to 8000, more preferably 2000 to 7000, and further preferably 3000 to 6000, for example. The mass average molecular weight of 2000 or more allows a sufficient molecular chain length to be obtained, which in turn provides a sufficient flexibility to the cured product. The mass average molecular weight of 7000 or less is preferable because it prevents the workability during application from deteriorating due to a too high viscosity of the composition, and allows a sufficient reactivity to be maintained, resulting in a sufficient curing.

Regarding (B) Acrylic Functional Group-containing Compound of Specific Structure The (B) component in the present invention is not particularly limited as long as it is a compound represented by the following chemical formula (1), which has three or more (meth)acryl groups in molecule and has a repeating structural unit of ethylene glycol in a main chain backbone. Commercial products of such a compound include Sartomer SR-3515, Sartomer SR-415, Sartomer SR-444, Sartomer SR-454, Sartomer SR-499, Sartomer SR-502, Sartomer CD-501, Sartomer SR-9035, and Sartomer (available from Tomoe Industries Co., Ltd.); Light Acrylate TMP-A, and Light Acrylate PE-3A (available from Kyoeisha Chemical Co., Ltd.); A-TMM, and A-TMPT (available from Shin-Nakamura Chemical Co., Ltd.); Aronix M-309, Aronix M-321, and Aronix M-350 (available from Toagosei Co., Ltd.); Miramer M300, Miramer M3130, Miramer M3160, Miramer M3190, and Miramer M360 (available from Toyo Chemicals Co., Ltd.); Fancryl FA-137M (available from Hitachi Chemical Co., Ltd.); and Neomer TA-401 and Neomer TA-505(available from Sanyo Chemical Industries Ltd.); and the like.

In the present invention, a compound wherein in the following chemical formula (1), x, y, and z are each independently an integer of 0 to 10 and satisfy x+y+z≤25 may be used. A compound in which x, y, and z are each desirably 0 to 5, and each more desirably 1 to 3, may preferably be used. Regarding R, a compound wherein R is a functional group selected from alkyl, aryl, haloalkyl, haloaryl, hydroxy alkyl, hydroxy haloalkyl groups each having 1 to 5 carbon atoms may be used. A compound where R is desirably an alkyl group having 1 to 3 carbon atoms may preferably be used. In addition, regarding R', a compound wherein R's are each a hydrogen atom or a monovalent functional group selected from alkyl and haloalkyl groups each having 1 to 3 carbon atoms, and may be the same or different, may be used. A compound wherein R's are each desirably a hydrogen atom or a methyl group may preferably be used. A compound where R's are each a methyl group or an ethyl group is preferable. Regarding n, a compound wherein n is an integer of 1 to 4 may be used, and a compound wherein n is desirably 1 to 3 may particularly preferably be used.

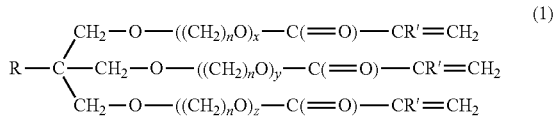

The role of the (B) component in the present invention is to provide adhesiveness to a nail to be coated with the curable resin composition for coating nails or to a base coat film applied on a nail, and to improve the photocuring reactivity owing to having an appropriate cross-linkable site, that is, to reduce the surface tack by reducing the oxygen inhibition. In the present invention, the amount of the (B) component to be added for appropriate functioning is preferably 1 to 35 parts by mass relative to 100 parts by mass of the (A) component, and 3 to 30 parts by mass, and more preferably 5 to 25 parts by mass from the viewpoints of flexibility and durability of the cured product. The (B) component in an amount of 1 parts by mass or more has small contribution to an improvement in photocuring reactivity, does not leave the surface tack, and also provides a sufficient adhesive force to the base and is thus not peeled off by stimulus. On the other hand, the (B) component in an amount of 35 parts by mass or less does not cause a too high reactivity and thus suppresses excessive increase in heat generation, and also does not increase the load applied to the human body during the curing on the nail.

Regarding (C) Compound Containing Acrylic Functional Group Having Aliphatic Ring Structure The (C) component in the present invention is a compound containing, in the same molecule, an acrylic functional group and a structure composed of a cycloalkyl group such as a cyclopropyl group, a cyclobutyl group, a cyclopentyl group, a cyclohexyl group, a cycloheptyl group, a cyclooctyl group, a cyclononyl group, a cyclodecyl group, a cycloundecyl group, or a cyclododecyl group, or a fused ring such as a dicyclopentanyl group, a 1-adamantyl group, a 2-adamantyl group, a norbornyl group, or an isobornyl group. Preferably, the ring structure and the acrylic functional group are desirably linked by a linking group having a smaller number of atoms than 10.

Moreover, in the present invention, it is further desirable to use, as such a compound, a (c-1) compound having an aliphatic ring structure and containing two or more acrylic functional groups and a (c-2) compound having an aliphatic ring structure and containing one acrylic functional group in combination. The (c-1) component includes cyclohexane dimethanol di(meth)acrylate, dimethylol tricyclodecane di(meth)acrylate, di(meth)acrylate modified with a hydrogenated bisphenol type epoxy resin, derivative compounds thereof, and the like. The (c-2) component includes isobornyl (meth)acrylate, 2-(meth)acryloyloxyethyl hexahydrophthalic acid, dicyclopentenyl oxyethyl (meth)acrylate, dicyclopentanyl oxyethyl (meth)acrylate, dicyclopentanyl (meth)acrylate, and cyclohexane dimethanol mono(meth) acrylate, and the like.

A composition ratio of the (c-1) component and the (c-2) component in the present invention is preferably 0.1 to 20 parts by mass of (c-2), and more preferably 1 to 10 parts by mass of (c-2), relative to 100 parts by mass of (c-1). Including the (c-1) component and the (c-2) component in the above composition ratio allows the present invention to achieve a favorable balance between the reactivity during the irradiation with the active energy ray and the properties of the cured product such as hardness. The (c-1) in an amount of 0.1 parts by mass or more provides a proper fluidity during the application, and does not impose unfavorable influence on the workability. On the other hand, the (c-1) in an amount of 20 parts by mass or less is preferable because the reactivity for the photocuring reaction is not lowered.

The role of the (C) component in the present invention is to adjust the hardness and the reactivity in the curable resin composition for coating nails. In the present invention, the amount of the (C) component to be added for appropriate functioning is preferably 15 to 75 parts by mass relative to 100 parts by mass of the (A) component, and 20 to 65 parts by mass, and more preferably 25 to 60 parts by mass, from the viewpoints of the flexibility of the cured product, the reactivity, and the workability during the application. The (C) component in an amount of 15 parts by mass or more provides a proper hardness to the cured product, does not cause a too high reactivity of the composition, and eliminates the possibility of burn injury due to heat generation.

On the other hand, the (C) component in an amount of 75 parts by mass or less does not excessively increase the hardness of the cured product, and allows a sufficient adhesiveness to the base to be maintained.

Regarding (D) Compound Containing Acrylic Functional Group Having Aliphatic Chain Structure The (D) component in the present invention is a compound containing, in the same molecule, an acrylic functional group and a chain alkyl group such as an ethyl group, a propyl group, a butyl group, a pentyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, or an icosyl group, and may have a side chain in the chain alkyl group. Here, the side chain is a hydrocarbon group having 1 to 5 carbon atoms, or a halogen atom.

The role of the (D) component in the present invention is to adjust the fluidity and the reactivity in the curable resin composition for coating nails. The (D) component does not have a higher reactivity than the (B) component and thus reduces the heat generated during the reaction, and also has a more flexible structure than the (C) component and can thus provide a proper flexibility to the cured product. In the present invention, the amount of the (D) component to be added for appropriately functioning is preferably 1 to 35 parts by mass relative to 100 parts by mass of the (A) component, and 1.5 to 25 parts by mass, and more preferably 3 to 20 parts by mass, from the viewpoints of the reactivity, the flexibility of the cured product, and the workability during the application. The (D) component in an amount of 1 part by mass or more provides a proper flexibility to the composition, and maintains a sufficient fluidity, so that the workability is not lowered. On the other hand, the (D) component in an amount of 35 parts by mass or less maintains the reactivity of the composition, and thus allows the composition to be appropriately cured on the nail, and does not cause a surface tack due to oxygen inhibition.

As the (D) component favorably usable in the present invention, from the viewpoints of the reactivity and the fluidity of the composition, the length of the aliphatic chain is preferably in a range of C6 to C20, and more preferably C8 to C15, and also, the number of the acrylic functional group is preferably one, that is, the acrylic functional group is preferably monofunctional. Specific compounds include hexyl (meth)acrylate, heptyl (meth)acrylate, 2-ethylhexyl methacrylate, octyl (meth)acrylate, nonyl (meth)acrylate, isononyl (meth)acrylate, isononyl (meth)acrylate, isodecyl (meth)acrylate, decyl (meth)acrylate, undecyl (meth)acrylate, lauryl (meth)acrylate, tridecyl (meth)acrylate, tetradecyl (meth)acrylate, pentadecyl (meth)acrylate, and the like.

Regarding (E) Photopolymerization Initiator

The (E) component in the present invention is a compound that is activated by an active energy ray such as a visible light, an ultraviolet ray, an X ray, a gamma ray, or an electron beam, and is capable of polymerizing acrylic functional groups contained in the (A) to (D) components. As the compound, a publicly-known commercial product may be used. For example, such publicly-known commercial products includes Irgacure 184, Irgacure 819, Irgacure 651, Irgacure 2959, Irgacure 907, Irgacure 127, Irgacure 369, Irgacure 379, Irgacure OXE 01, Irgacure OXE 02, Lucirin TPO, and Darocur 1173(available from BASF SE), Esacure 1001M and Esacure KIP 150(available from LAMBERTI S.P.A.), SpeedCure TPO, SpeedCure BEM, SpeedCure MBF, SpeedCure PDO, SpeedCure BMS, and SpeedCure PBZ (available from LAMBSON LIMITED), Suncure 84 (available from Chemark Chemical Co., Ltd.), benzophenone, and the like. These photopolymerization initiators may be used alone or may be used in combination of two or more of them. Combining compounds that absorb wavelength regions of visible light and ultraviolet ray, respectively, is more preferable because it can expand the choice of the usable activation energy light source.

In the present invention, the amount of the (E) component for appropriately functioning is preferably 0.5 to 13.5 parts by mass relative to 100 parts by mass of the (A) component, and more preferably 1.0 to 12 parts by mass and further preferably 1.2 to 11 parts by mass, from the viewpoints of the storability and the colorability of the cured product. This is preferable because the (E) component in an amount of 0.5 parts by mass or more exhibits a sufficient photopolymerizability, and the (E) component in an amount of 13.5 parts by mass or less maintains the stability during storage, and does not make the cured product likely to be colored.

Moreover, in the present invention, a component for adding proper properties to the curable resin composition may be added as needed besides the (A) to (E). For example, a reactive or non-reactive diluent, an antioxidant, a thickener, a surfactant, a tackifier, a frame retardant, a stabilizer, a pigment, and the like may be favorably used. In particular, adding a thickener such as a fumed silica can provide favorable thixotropy and viscosity to enhance the workability during the application.

Furthermore, the curable resin composition for coating nails of the present invention can be used for cover coating application as a top coating layer or an intermediate coating layer by being applied and cured on a base coating layer formed on a nail in advance. Here, the nail may be an artificial nail or a natural nail, but is preferably human nails and/or nails of mammals other than humans. In addition, as the composition forming the base coating layer, a photo-radical polymerizable compound made of a reactive acrylic oligomer having a high flexibility such as urethane acrylate, a hydroxyl group-containing acrylic monomer having a high adhesion to nails, a photo-radical polymerization initiator, and the like is used. Such a composition has a favorable adhesion to nails and also a favorable followability to deformation and the like of nails because of its flexibility and adhesiveness, but on the other hand, has a problem that the composition is easily chipped and peeled off by stimulus from the outside because of its flexibility.

As a material for forming such a base coating layer, a composition containing a radical functional group-containing oligomer can be used. As the radical functional group-containing oligomer, polyether acrylates, polyester acrylates, polyurethane acrylates, polyester urethane acrylates, polyether urethane acrylates, polycarbonate urethane acrylates and the like can be used, for example, and an oligomer of a polyurethane-based acrylate is preferably used from the viewpoints of the flexibility, the followability, and the like of the cured product layer. Moreover, a top coating layer made of components that form a harder coating may be coated and cured on a cover coating layer of the present invention such that the curable resin composition for coating nails of the present invention is used for cover coating as an intermediate coating layer. Such a multilayer coating can achieve both the adhesion and the followability to nails and the durability against stimulus from the outside at a higher level.

Although the present invention will be described below in more detail based on Examples, the present invention is not limited to these Examples at all.

EXAMPLES

Evaluation Methods

The properties of the curable resin composition for coating nails in Examples were evaluated by the following methods, respectively.

Hardness

Test pieces each obtained by placing three layers of cured products of the curable resin composition each having a thickness of 1 mm were used, and were evaluated for the hardness property by measuring a hardness value specified in JIS-K-6253 using a shore durometer (available from ASKER, Type-D) under an environment of 25° C. and 65 RH %. Here, an appropriate value for the hardness value as the composition to be coated on nails was set in a range of D70 to D75. Note that the test pieces of the cured products were each prepared by applying the curable resin composition onto a flat glass surface, and was irradiated with an ultraviolet ray using an ultraviolet ray irradiation device with a transporting device (available from Ushio Inc., UVC-025165) such that the accumulated amount of light was 3000 mJ/cm$^2$.

Surface Tack

Test pieces of cured products prepared by the same method as those prepared for the hardness evaluation were used, and the surface of each test piece after cure was evaluated by a finger touch with a finger tip which was degreased using ethanol. The evaluation was conducted such that a test piece which was felt as having tack even slightly by the finger tip was denoted with "NG" as being failed, while a test piece which was not felt as having tack was denoted with "OK" as being passed.

External Appearance

Test pieces of cured products prepared by the same method as those prepared for the hardness evaluation were used, and each test piece after cure was evaluated visually for the degree of coloration. As the criteria for the evaluation, a test piece having a color tone of colorless and transparent to a very light yellow was denoted with "OK" as being passed, while a test piece having a color tone of yellow to brown was denoted with "NG" as being failed.

Heat Generation

A curable resin composition was applied in a thickness of 0.1 mm on the entire surface of a nail of a test subject which was degreased with ethanol, was irradiated with an ultraviolet ray for 120 seconds using a sport UV irradiation device (available from Muraki & Co., Ltd., Superior UV Lamp) and thereafter was irradiated with light having a wavelength of 405 nm for 10 seconds using a spot LED irradiation device (available from Natural Field Supply Inc., Personal LED Light). Each curable resin composition was evaluated by 10 test subjects through a body sensory test, for heat generated from a applied portion when the irradiation was conducted on the surface of the nail coated with the curable resin composition. A curable resin composition with which 5 or more among the ten test subjects felt even little heat was denoted with "NG" as being failed, while a curable resin composition with which 0 to 4 test subjects felt heat was denoted with "OK" as being passed.

Overcoatability

The overcoatability was evaluated as an evaluation for checking the properties of the curable resin composition for coating nails of the present invention when the curable resin composition for coating nails is used as an intermediate coat or a top coat of a multilayer coating. Test pieces were prepared by the following method.

1. A base coat composition comprising: 60% of a urethane acrylate; 20% of a monofunctional acrylic functional group-containing compound containing a hydroxyl group; 5% of a photo-radical polymerization initiator having absorption wavelengths in ultraviolet ray and visible light regions; and the balance of a silane coupling agent, a hydrophobic fumed silica, a reactive diluent, a coloring agent of red, and the like was applied with a brush in a film thickness of 100 μm onto a PET film of 1.200 μm, and was irradiated with an ultraviolet ray using an ultraviolet ray irradiation device with a transporting device (available from Ushio Inc., UVC-02516S) such that the accumulated amount of light was 3000 mJ/cm$^2$, thereby forming a base coating layer.

2. The curable resin composition for coating nails having compositions described in Table 1 was applied with a brush in a film thickness of 300 μm onto the base coating layer, and was irradiated with an ultraviolet ray under the same conditions as above, thereby forming an intermediate coat layer of the present invention.

3. A top coat composition comprising: 60% of a urethane acrylate; 15% of a trifunctional acrylic functional group-containing compound; 20% of a monofunctional acrylic functional group-containing compound containing an alicyclic group; 4.5% of a photo-radical polymerization initiator having absorption wavelengths in ultraviolet ray and visible light regions; and the balance of a fumed silica, a plasticizer, and a coloring agent of blue, and the like was applied with a brush in a film thickness of 300 μm on the intermediate coating layer, and was irradiated with an ultraviolet ray under the same conditions as above, thereby forming a top coating layer. Note that each layer was applied such that the area of application was 50 mm$^2$ or more.

4. As shown in FIG. 1, the PET film was bent by 180° at a substantially center portion of the applied surface of the PET film on which the multilayer coating layer was formed (1-B). The bent portion was returned to the initial position, and the same portion was then bent by 180° in the opposite direction (1-C), and was returned to the initial position again. The series of this operation was counted as one set, and 10 sets were repeated in total.

5. Here, the overcoatability was evaluated by visually checking the bent portion to see whether peeling occurred. A test piece in which peeling was found in the intermediate coat layer even slightly at the bent portion was denoted with "NG" as being failed for the overcoatability, while a test piece in which no peeling was found was denoted with "OK" as being passed. In this event, the peeling of the intermediate coating layer was determined according to the difference in color of the layers.

Results of the evaluations conducted by the above measuring methods are described in the following table together with constitutions of the respective compositions used in Examples and Comparative Examples. Note that the blending compositions in the table were all described in part by mass. Note that the total evaluation was denoted with "o" if the properties were favorable, or denoted with "×" if the properties were not favorable, by collectively considering the hardness, the surface tack, the external appearance, the heat generation, and the overcoatability.

TABLE 1

| Composition | Trade Name | Example 1 | Example 2 | Example 3 | Example 4 | Comparative Example 1 | Comparative Example 2 | Comparative Example 3 | Comparative Example 4 | Comparative Example 5 | Comparative Example 6 |
|---|---|---|---|---|---|---|---|---|---|---|---|
| (A) | UV3310B | 100 | 100 | 100 | 100 | 100 | 100 | 100 | 100 | 100 | 100 |
| (B) | SR-454 | | | 8.0 | | | | | | | |
| | SR-499 | | | | 8.0 | | | | | | |
| | SR-502 | 8.0 | 15 | | | 0 | 8.0 | 15 | 0 | | |
| Comparative (B) | SR-247 | | | | | | | | | 8.0 | |
| | SR-268 | | | | | | | | | | 8.0 |
| (c-1) | DCP-A | 45 | 36 | 45 | 45 | 52 | 45 | 45 | 45 | 45 | 45 |
| (c-2) | IB-X | 2.0 | 2.0 | 2.0 | 2.0 | 2.0 | 2.0 | 2.0 | 2.0 | 2.0 | 2.0 |
| (D) | INAA | 8.0 | 8.0 | 8.0 | 8.0 | 8.0 | 8.0 | 0 | 16 | 8.0 | 8.0 |
| (E) | TPO | 5.0 | 5.0 | 5.0 | 5.0 | 5.0 | 9.0 | 5.0 | 5.0 | 5.0 | 5.0 |
| | Suncure 84 | 5.0 | 5.0 | 5.0 | 5.0 | 5.0 | 5.0 | 5.0 | 5.0 | 5.0 | 5.0 |
| Other | AEROSIL 200 | 0.5 | 0.5 | 0.5 | 0.5 | 0.5 | 0.5 | 0.5 | 0.5 | 0.5 | 0.5 |
| | Total | 173 | 171 | 173 | 173 | 172 | 177 | 172 | 173 | 173 | 173 |
| Property Evaluation Results | Hardness | D75 | D70 | D74 | D73 | D83 | D73 | D77 | D74 | D73 | D73 |
| | Surface Tack | OK | OK | OK | OK | OK | OK | OK | NG | NG | NG |
| | External Appearance | OK | OK | OK | OK | OK | NG | OK | OK | OK | OK |
| | Heat Generation | OK | OK | OK | OK | OK | OK | NG | OK | OK | OK |
| | Overcoatability | OK | OK | OK | OK | NG | OK | OK | OK | OK | OK |
| | Total Evaluation | ○ | ○ | ○ | ○ | x | x | x | x | x | x |

Product Names Described in Table 1
(A) Component
UV3310B: trade name "UV3310B", polycarbonate-based urethane acrylate, available from The Nippon Synthetic Chemical Industry Co., Ltd., mass average molecular weight: approximately 5,000 (B) Component: a compound having a chemical structure of the following general formula (Chem. 1)

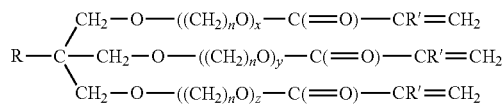

wherein x, y, and z are each independently an integer of 0 to 10 and satisfy $x+y+z \leq 25$, R is a functional group selected from alkyl, aryl, haloalkyl, haloaryl, hydroxy alkyl, hydroxy haloalkyl groups each having 1 to 5 carbon atoms, R's each are a hydrogen atom or a functional group selected from alkyl and haloalkyl groups each having 1 to 3 carbon atoms and may be the same or different, and n is an integer of 1 to 4.

SR-454: Sartomer SR-454, ethoxylated trimethylolpropane triacrylate, where $x=y=z=1$, $R=C_2H_5$, $R'=H$, $n=2$ in the above chemical formula (Chem. 1), available from Tomoe Industries Co., Ltd.

SR-499: Sartomer SR-499, ethoxylated trimethylolpropane triacrylate, where $x=y=z=2$, $R=C_2H_5$, $R'=H$, $n=2$ in the above chemical formula (Chem. 1), available from Tomoe Industries Co., Ltd.

SR-502: Sartomer SR-502, ethoxylated trimethylolpropane triacrylate, where $x=y=z=3$, $R=C_2H_5$, $R'=H$, $n=2$ in the above chemical formula (Chem. 1), available from Tomoe Industries Co., Ltd.

Comparative Components of (B)
SR-247: Sartomer SR-247, neopentyl glycol diacrylate, available from Tomoe Industries Co., Ltd.

SR-268: Sartomer SR-268, tetraethylene glycol diacrylate, available from Tomoe Industries Co., Ltd.

(c-1) Component
DCP-A: Light Acrylate DCP-A, dimethylol tricyclodecane diacrylate, available from Kyoeisha Chemical Co., Ltd.

(c-2) Component
IB-X: Light Ester IB-X, isobornyl methacrylate, available from Kyoeisha Chemical Co., Ltd.

(D) Component
INAA: isononyl acrylate, available from Osaka Organic Chemical Industry Ltd.

(E) Component
TPO: SpeedCure TPO, 2,4,6-trimethylbenzoyl diphenyl phosphineoxide, available from LAMBSON Limited Suncure 84: 1-hydroxycyclohexyl phenyl ketone, available from Chemark Chemical Co., Ltd.

(Other) Component
AEROSIL 200: a hydrophilic fumed silica having a specific surface area of $200\pm25$ $m^2/g$, available from Evonik Industries In Examples 1 to 4, the properties were evaluated for compositions with formulations in which proper components were combined in proper composition ratios in the present invention. In these Examples, all of the cured products formed by curing the respective compositions had hardness values in a range of D70 to D75, and exhibited favorable results in the evaluations of the surface tack, the external appearance, the heat generation, and the overcoatability.

On the other hand, in Comparative Examples 1 to 6, the properties were evaluated for compositions and the like with formulations in which non-proper components were used, or in which proper components were combined in non-proper composition ratios in the present invention. Comparative Example 1 was a composition that did not contain the (B) component, which is an essential component of the present invention, and was compensated for that with (c-1). In the results of property evaluations of the composition, although there were no problems in the properties of the surface tack, the external appearance, and the heat generation, the hardness value significantly exceeded the proper range. In addition, in the overcoatability evaluation, peeling occurred between the intermediate coat layer of the present invention and the base coating layer. This is assumed to be because the composition did not contain the (B) component, which is a structure having a flexible backbone structure and many cross-linkable portions, and had an increased amount of (c-1), which is a rigid backbone structure, and this lowered the followability of the cured product to the acrylic resin layer composed mainly of urethane acrylate, which is the base coating layer, and also increased the hardness of the cured product. On the other hand, it is assumed that although the increased amount of the (c-1) component has a smaller number of functional groups than (B) but has a high reactivity, the (c-1) component was unlikely to undergo oxygen inhibition, so that the surface tack was not lowered.

Comparative Example 2 was a composition with a formulation containing the (E) component in an amount in the proper range or more. Although there were no problems in any of the properties of the hardness, the surface tack, the heat generation, and the overcoatability, the degree of coloration was large, so that the favorability of the external appearance was degraded.

Comparative Example 3 was a composition that did not contain the (D) component and was compensated for that with (B). In the results of the property evaluations of the composition, although there were no problems in any of the properties of the surface tack, the external appearance, and the overcoatability, the heat generation was large and the hardness value also exceeded the proper range. This is assumed to be because since the composition did not contain the (D) component, which is a monofunctional acrylic monomer, the number of functional groups in turn increased in the entire system, which increased the degree of cross-linkability, and the reactivity is thus increased to increase the heat generation, and also increased the hardness of the cured product.

Comparative Example 4 was a composition that did not contain the (B) component and was compensated for that with (D). In the results of the property evaluations in the composition, there were no problems in any of the properties of the hardness, the external appearance, the heat generation, and the overcoatability, the surface tack was poor. This is assumed to be because since the composition did not contain the (B) component, and contain an increased amount of the (D) component, which is a monofunctional acrylic monomer, the number of functional groups in turn decreased in the entire system, which lowered the reactivity, and as a result, the composition was influenced by oxygen inhibition, so that the surface curability was lowered and the surface tack was degraded.

Both Comparative Examples 5 and 6 were compositions with formulations using non-proper components as the (B) component. Comparative Example 5 had a formulation using SR-247, which is a compound having an aliphatic chain backbone and acrylic functional groups at both terminals, in place of the (B) component. Comparative Example 6 was a composition having a formulation using SR-268, which is a compound having a flexible polyether backbone and acrylic functional groups at both terminals, in place of the (B) component. In each example, there were no problems in any of the properties of the hardness, the external appearance, the heat generation, and the overcoatability, but the surface tack was poor. It was acknowledged that even when the (B) is replaced with an acrylic functional compound having a flexible structure and being relatively similar to the (B), desired properties cannot be exhibited without a proper number of functional groups.

INDUSTRIAL APPLICABILITY

It is not easy to satisfy all the properties such as hardness, external appearance, surface tack (surface curability), heat generation, and overcoatability, which are required for a composition for coating nails. The curable resin composition for coating nails of the present invention, which satisfies all of these, is thus very useful in coating nails for the purposes of protection, decoration, reinforcement, and the like of the nails.

REFERENCE SIGNS LIST a: PET film
b: multilayer coating layer
c: bending position

The invention claimed is:

1. A curable resin composition for coating nails, comprising:
   (A) 100 parts by mass of a compound having a urethane structure, having a polyester backbone, and containing acrylic functional groups at both terminals of a molecular chain;
   (B) 1 to 35 parts by mass of an acrylic functional group-containing compound having the following structure

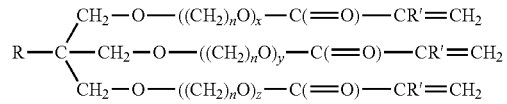

wherein x, y, and z are each independently an integer of 0 to 10 and satisfy x+y+z≤25, R is a functional group selected from alkyl, aryl, haloalkyl, haloaryl, hydroxy alkyl, hydroxy haloalkyl groups each having 1 to 5 carbon atoms, R's are each a hydrogen atom or a functional group selected from alkyl and haloalkyl groups each having 1 to 3 carbon atoms, and may be the same or different, and n is an integer of 1 to 4;
   (C) 15 to 75 parts by mass of
      (c-1) a compound having an aliphatic ring structure and containing two or more acrylic functional groups; and
      (c-2) a compound having an aliphatic ring structure and containing one acrylic functional group;
   (D) 1 to 35 parts by mass of a compound containing an acrylic functional group having an aliphatic chain structure; and
   (E) 0.5 to 13.5 parts by mass of a photopolymerization initiator.

2. The curable resin composition for coating nails of claim 1, wherein the (A) component comprises an acrylic functional group-containing compound having the polyester backbone and a mass average molecular weight of 1000 to 8000.

3. The curable resin composition for coating nails of claim 1, wherein in the structure of the compound (B), x, y, and z are each independently an integer of 0 to 5, R is an alkyl group having 1 to 3 carbon atoms, R' is a hydrogen atom or a methyl group, and n is an integer of 1 to 3.

4. The curable resin composition for coating nails of claim 1, wherein the length of the aliphatic chain of the (D) component is in the range of C6 to C20.

5. The curable resin composition for coating nails of claim 1, wherein the photopolymerization initiator is a compound that is activated by a visible light and/or an ultraviolet ray.

6. The curable resin composition according to claim 1, wherein the curable resin composition is a cover coating layer for nails.

7. A cover coating layer formed by applying and curing a curable resin composition for coating nails comprising:
(A) 100 parts by mass of a compound having a urethane structure, having a polyester backbone, and containing acrylic functional groups at both terminals of a molecular chain;
(B) 1 to 35 parts by mass of an acrylic functional group-containing compound having the following structure

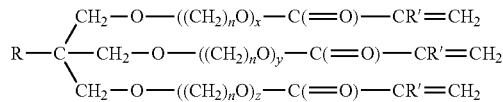

wherein x, y, and z are each independently an integer of 0 to 10 and satisfy $x+y+z \leq 25$, R is a functional group selected from alkyl, aryl, haloalkyl, haloaryl, hydroxy alkyl, hydroxy haloalkyl groups each having 1 to 5 carbon atoms, R's are each a hydrogen atom or a functional group selected from alkyl and haloalkyl groups each having 1 to 3 carbon atoms, and may be the same or different, and n is an integer of 1 to 4;
(C) 15 to 75 parts by mass of
  (c-1) a compound having an aliphatic ring structure and containing two or more acrylic functional groups; and
  (c-2) a compound having an aliphatic ring structure and containing one acrylic functional group;
(D) 1 to 35 parts by mass of a compound containing an acrylic functional group having an aliphatic chain structure; and
(E) 0.5 to 13.5 parts by mass of a photopolymerization initiator.

8. The cover coating layer according to claim 7, wherein the cover coating layer is coated on a base coating layer formed on a nail in advance.

9. The cover coating layer according to claim 7, wherein the (A) component comprises an acrylic functional group-containing compound having the polyester backbone and a mass average molecular weight of 1000 to 8000.

10. The cover coating layer according to claim 7, wherein in the structure of the compound (B), x, y, and z are each independently an integer of 0 to 5, R is an alkyl group having 1 to 3 carbon atoms, R' is a hydrogen atom or a methyl group, and n is an integer of 1 to 3.

11. The cover coating layer according to claim 7, wherein the length of the aliphatic chain of the (D) component is in a range of C6 to C20.

12. The cover coating layer according to claim 7, wherein the photopolymerization initiator is a compound that is activated by a visible light and/or an ultraviolet ray.

13. A nail coating method, comprising the steps of:
(1) applying a curable resin composition for coating nails onto a nail, the curable resin comprising:
(A) 100 parts by mass of a compound having a urethane structure, having a polyester backbone, and containing acrylic functional groups at both terminals of a molecular chain;
(B) 1 to 35 parts by mass of an acrylic functional group-containing compound having the following structure

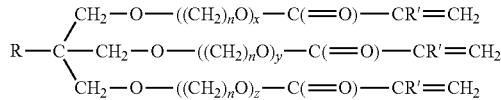

wherein x, y, and z are each independently an integer of 0 to 10 and satisfy $x+y+z \leq 25$, R is a functional group selected from alkyl, aryl, haloalkyl, haloaryl, hydroxy alkyl, hydroxy haloalkyl groups each having 1 to 5 carbon atoms, R's are each a hydrogen atom or a functional group selected from alkyl and haloalkyl groups each having 1 to 3 carbon atoms, and may be the same or different, and n is an integer of 1 to 4;
(C) 15 to 75 parts by mass of
  (c-1) a compound having an aliphatic ring structure and containing two or more acrylic functional groups; and
  (c-2) a compound having an aliphatic ring structure and containing one acrylic functional group;
(D) 1 to 35 parts by mass of a compound containing an acrylic functional group having an aliphatic chain structure; and
(E) 0.5 to 13.5 parts by mass of a photopolymerization initiator; and
(2) curing the applied curable resin composition by applying an active energy ray to the curable resin composition, forming a cured layer.

14. The nail coating method according to claim 13, wherein the nail to which the curable resin composition for coating nails is applied is coated with a base coating layer in advance, and
the step (1) of applying the curable resin composition for coating nails includes applying the curable resin composition for coating nails onto the nail coated with the base coating.

15. The nail coating method according to claim 13, wherein the (A) component comprises an acrylic functional group-containing compound having the polyester backbone and a mass average molecular weight of 1000 to 8000.

16. The nail coating method according to claim 13, wherein in the structure of the compound (B), x, y, and z each independently an integer of 0 to 5, R is an alkyl group having 1 to 3 carbon atoms, R' is a hydrogen atom or a methyl group, and n is an integer of 1 to 3.

17. The nail coating method according to claim 13, wherein the length of the aliphatic chain of the (D) component is in a range of C6 to C20.

18. The nail coating method according to claim 13, wherein the photopolymerization initiator is a compound that is activated by a visible light and/or an ultraviolet ray.

* * * * *